United States Patent [19]

Hirai et al.

[11] Patent Number: 5,100,457
[45] Date of Patent: Mar. 31, 1992

[54] OXAZOLIDINEDIONE COMPOUNDS, THE PROCESS FOR PREPARING THE SAME AND HERBICIDAL COMPOSITION CONTAINING THE SAME

[75] Inventors: Kenji Hirai, Kanagawa; Atsuko Fujita, Chiba; Hiroshi Sato, Chiba; Hiroaki Hirose, Chiba; Masahiro Yokota, Chiba; Shoin Nagato, Tokyo, all of Japan

[73] Assignees: Sagami Chemical Research Center, Tokyo; Chisso Corporation, Osaka; Kaken Pharmaceutical Co., Ltd., Tokyo, all of Japan

[21] Appl. No.: 635,379

[22] Filed: Jan. 3, 1991

Related U.S. Application Data

[63] Continuation of Ser. No. 377,138, Jul. 10, 1989, abandoned.

[30] Foreign Application Priority Data

Feb. 17, 1989 [JP] Japan .................................. 1-37833
Feb. 17, 1989 [JP] Japan .................................. 1-37834

[51] Int. Cl.$^5$ .................... C07D 263/44; A01N 43/74
[52] U.S. Cl. ......................................... 71/88; 548/226
[58] Field of Search ............................. 548/226; 71/88

[56] References Cited

U.S. PATENT DOCUMENTS

| 2,928,840 | 3/1960 | Shapiro ............................... 548/226 |
| 3,201,410 | 8/1965 | Morel et al. ......................... 548/226 |
| 3,703,526 | 11/1972 | Sato et al. ........................... 548/226 |
| 3,966,750 | 6/1976 | Mangold et al. ..................... 548/226 |
| 3,995,049 | 11/1976 | Mangold et al. ..................... 548/226 |
| 4,818,272 | 4/1989 | Hirai et al. .......................... 548/226 |

FOREIGN PATENT DOCUMENTS

| 0241559 | 10/1987 | European Pat. Off. . |
| 0024870 | 2/1979 | Japan ................................. 514/376 |
| 0203372 | 8/1989 | Japan ................................. 548/226 |
| 0085629 | 3/1990 | Japan ................................. 548/226 |
| 273822 | 9/1977 | U.S.S.R. . |

OTHER PUBLICATIONS

Bodenitausen, "Guide to the Application of the Paris Convention for the Protection of Industrial Property", Birpi, Geneva 1968, pp. 45–46.

*Primary Examiner*—Donald G. Daus
*Attorney, Agent, or Firm*—Nixon & Vanderhye

[57] ABSTRACT

An oxazolidinedione compound represented by the formula (I):

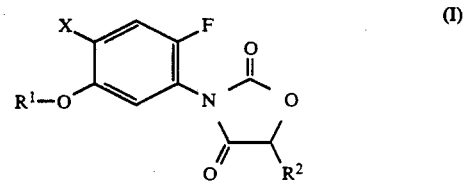

wherein $R^1$ represents a hydrogen atom, an alkyl group having 1 to 5 carbon atoms, a cycloalkyl group having 3 to 5 carbon atoms, an alkenyl group having 3 to 5 carbon atoms, an alkynyl group having 3 to 5 carbon atoms or an alkoxycarbonyl group having 1 or 2 carbon atoms in the alkyl moiety thereof, $R^2$ represents an alkyl group having 3 to 5 carbon atoms or a cycloalkyl group having 3 to 5 carbon atoms, and X represents a chlorine atom or a fluorine atom; a process for preparing the same; and a herbicidal composition comprising the oxazolidinedione compound as an active component are disclosed. The above oxazolidinedione compounds exhibit a high selectivity for useful crop plants and a strong herbicidal activity with respect to various noxious weeds.

4 Claims, No Drawings

OXAZOLIDINEDIONE COMPOUNDS, THE PROCESS FOR PREPARING THE SAME AND HERBICIDAL COMPOSITION CONTAINING THE SAME

This is a continuation of application Ser. Nos. 07/377,138, filed July 10, 1989, now abandoned.

BACKGROUND OF THE INVENTION

This invention relates to novel oxazolidinedione compounds having both a potent herbicidal activity against various strongly weeds and a high selectivity for useful crop plants; a process for preparing the oxazolidinedione compounds; and a herbicidal composition containing the oxazolidinedione compound as an active component.

DESCRIPTION OF THE PRIOR ART

Recently, in the research of developing a new herbicidal composition, a continual search for compounds which not only exhibit no phytotoxicity against useful crop plants and an excellent selectivity to show a strong herbicidal activity only against noxious weeds but also exhibit the desired herbicidal effect at a possible low dose from the standpoint of protection from an environmental pollution and provide a high safety is being carried out. Some compounds which have such characteristics have been practically used, nevertheless there is still a strong need for novel herbicidal compounds which have higher performance.

Most of the conventionally known compounds possessing an oxazolidinedione ring as a fundamental structure exhibit a mainly fungicidal activity, and oxazolidinedione derivatives such as vinchlozoline, etc., in fact, are used as an active component of fungicidal compositions for agricultural or gardening usage (U.S. Pat. No. 3,995,049 and U.S. Pat. No. 3,966,750).

On the other hand, oxazolidinedione derivatives, for example, compounds as described in U.S. Pat. No. 3,201,410 and U.S. Pat. No. 2,928,840 are known to have a herbicidal activity, but their herbicidal activity is very weak and they are far from practical herbicidal composition as an active component.

DETAILED DESCRIPTION OF THE INVENTION

The present inventors have extensively studied in order to develop novel herbicidal agents which exhibit an effective herbicidal activity at a low dose and a high selectivity for useful crop plants, and they synthesized oxazolidinedione compounds having various substituted groups and investigated their biological activities in order to discover novel compounds which have much improved herbicidal characteristics. As a result they found that herbicidal activity increase dramatically when 2-fluoro-4-halogeno-5-alchoxyphenyl residue is introduced on the nitrogen atom at 3 position of the oxazolidinedione ring and additionally that oxazolidine compounds having an alkyl group of 3 to 5 carbon chain or a cycloalkyl group substituted on the 5 position of the oxazolidinedione ring (herein described as the compounds of this invention) as shown in the following formula (I):

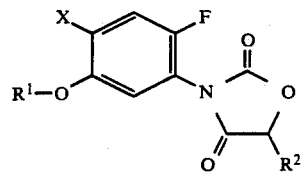

(wherein $R^1$ represents a hydrogen atom, alkyl group having 1 to 5 carbon atoms, a cycloalkyl group having 3 to 5 carbon atoms, an alkenyl group having 3 to 5 carbon atoms or an alkynyl group having 3 to 5 carbon atoms; $R^2$ represents an alkyl group having 3 to 5 carbon atoms or a cycloalkyl group having 3 to 5 carbon atoms; and X represents a chlorine atom or a fluorine atom) exhibit both a strong herbicidal activity against various weeds and high selectivity for useful crop plants. On this basis they completed the present invention.

Especially the compounds of this invention show a more potent herbicidal activity at a lower dose than conventional herbicidal agents. That is, when used in the paddy field even at a low dose, the compounds of this invention exhibit a very strong herbicidal activity against annual weed such as Echinochloa Crus-galli, Monochoria vaginalis, Ammania mutiflora, etc. When used on fields, the compounds of this invention also exhibit an effective withering activity on field weeds such as Amaranthas lividus, Digitaria adscendens, Setaria viridis, Chenopodium album, Polygonum longisetum, Amaranthus viridis, Portulaca oleracea, Plantago asiatica, etc. Furthermore, the compounds of this invention possess an excellent selectivity for useful crop plants such as corn, soybean, etc. and exhibit a herbicidal activity against graminaceous weeds such as Echinochloa Crus-galli, Igitaria sanguinalis, Staria viridis, etc., but these compounds show substantially no phytotoxicity to graminaceous crops such as transplanted paddy rice, wheat, corn, etc. In addition, these compounds show substantially no phytotoxicity to crops other than graminaceous crops such as soybean, cotton, etc.

Compounds having a similar structure to the compounds of this invention, for example, the compounds of U.S. Pat. No. 3,201,410 and U.S. Pat. No. 2,928,840 as described above, are known. However, the present inventors synthesized these compounds (Control Compounds 1 and 2 as described below) and evaluated their herbicidal effect finding that their herbicidal activity is much weaker than that of the compounds of this invention (refer to Experimental Examples as described below). In addition, the compounds as described in U.S.S.R. Patent No. 273,822 and U.S. Pat. No. 4,818,272 are known as oxazolidinedione compounds having a herbicidal activity but these compounds are clearly different from the compounds of this invention in that they have a substituted methylidene group at the 5 position of the oxazolidinedione ring.

According to this invention, novel oxazolidinedione compounds as shown in the formula (I) can be prepared by various processes, for example, by the following reactions.

Process 1

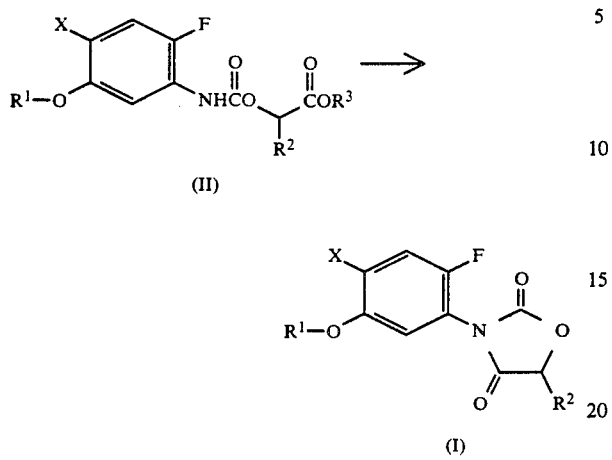

(wherein $R^1$, $R^2$ and X are as defined above and $R^3$ represents an alkyl group having 1 to 4 carbon atoms).

Process 2

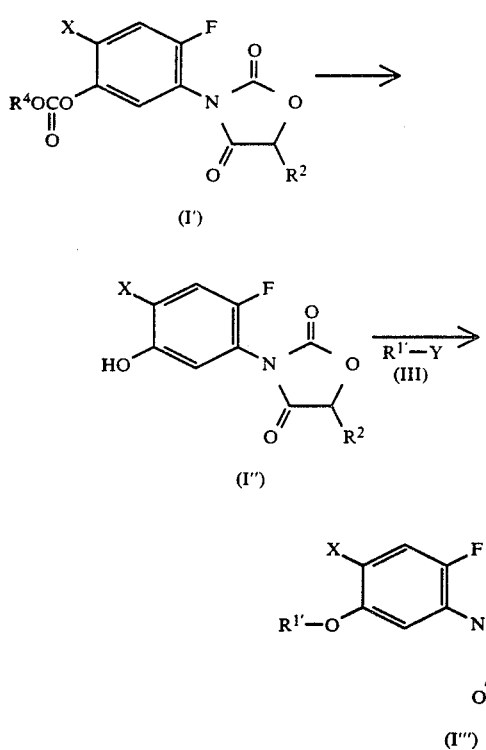

(wherein $R^2$ and X are as defined above; $R^{1'}$ represents an alkyl group having 1 to 5 carbon atoms or a cycloalkyl group having 3 to 5 carbon atoms, an alkenyl group having 3 to 5 carbon atoms or an alkynyl group having 3 to 5 carbon atoms; $R^4$ represents an alkyl group having 1 to 4 carbon atoms; and Y represents a leaving group).

Process 3

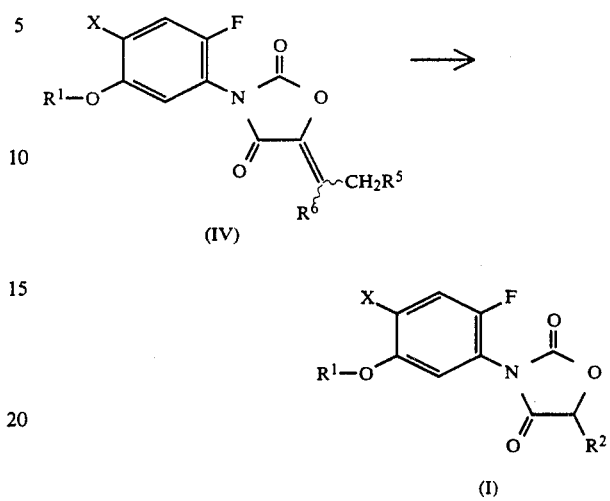

(wherein $R^1$, $R^2$ and X are as defined above; and $R^5$ and $R^6$ each independently represent a hydrogen atom or an alkyl group having 1 or 2 carbon atoms, or $R^5$ and $R^6$ can be joined together to form a polymethylene chain).

The starting materials represented by the formula (II) in the process for preparing the compounds of this invention are novel compounds, which can be prepared by various processes, for example, by the following reactions.

Process for Preparing the Starting Compounds 1

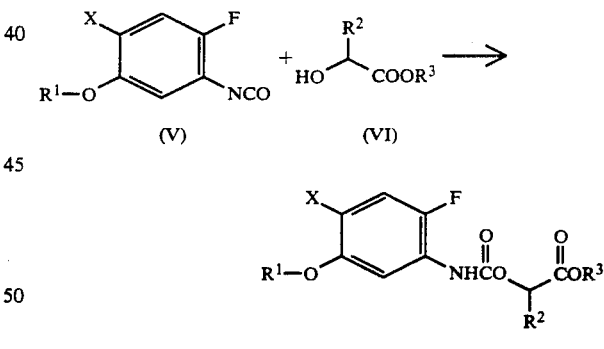

(wherein $R^1$, $R^2$, $R^3$ and X are as defined above).

Process for Preparing the Staring Compounds 2

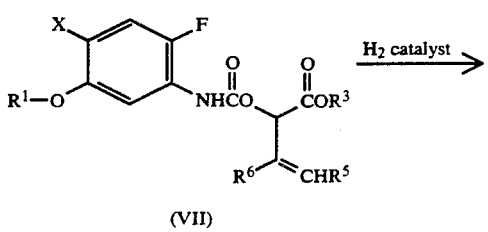

-continued

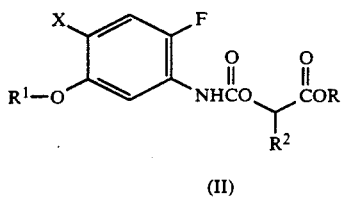

(II)

(wherein $R^1$, $R^2$, $R^3$, $R^5$, $R^6$ and X are as defined above).

In all the descriptions above and below, preferable examples and explanations for various definitions involved in the range of the present invention will be described below in detail.

Examples of an alkyl group having 1 to 5 carbon atoms which can be used in this invention, include a straight or branch chain alkyl group such as a methyl group, an ethyl group, a propyl group, an isopropyl group, a butyl group, a t-butyl group, a sec-butyl group, a pentyl group, a 3-pentyl group, etc.

Examples of a cycloalkyl group having 3 to 5 carbon atoms which can be used in this invention include a cyclic alkyl group such as a cyclopropyl group, a cyclobutyl group, a cyclopentyl group, etc.

Examples of an alkenyl group having 3 to 5 carbon atoms which can be used in this invention include a straight or branch alkenyl group such as an allyl group, a methallyl group, a crotyl group, a 2-butenyl group, a 3-butenyl group, a 1-methyl-2-butenyl group, a 2-pentenyl group, etc.

Examples of an alkynyl group having 3 to 5 carbon atoms which can be used in this invention include a straight or branch alkynyl group such as a propargyl group, a 1-methylpropargyl group, a 1,1-dimethylpropargyl group, a 1-ethylpropargyl group, a 2-methylpropargyl group, a 2-butynyl group, a 3-butynyl group, a 2-pentynyl group, a 3-pentynyl group, etc.

Preferable examples of "Y" as a leaving group which can be used in this invention include a halogen atom such as a fluorine atom, a chlorine atom, a bromine atom and an iodine atom and a substituted sulfonyloxy group such as a tolysulfonyloxy group, a phenylsulfonyloxy group, a methylsulfonyloxy group, etc.

The processes for preparing the oxazolidinedione compounds, that is, the compounds of this invention, represented by the formula (I) are explained below in detail.

Process 1

The compounds of this invention represented by the formula (I) can be prepared by subjecting a carbamic acid ester represented by the formula (II) to a cyclization reaction.

This reaction is typically carried out in the presence of a base. Examples of a preferable base which can be used include a tertiary amine such as triethylamine, tripropylamine, N-methylmorphorine, etc.; an aromatic amine such as pyridine, lutidine, etc.; an alkali metal alkoxide such as sodium methoxide, sodium ethoxide, potassium t-butoxide, etc.; a basic inorganic compound such as sodium carbonate, potassium carbonate, etc.; and a carboxylic acid metal salt such as sodium acetate, potassium acetate, lithium acetate, etc.

This reaction is carried out in an organic solvent. Examples of a preferred organic solvent which can be used include an aromatic solvent such as benzene, toluene, xylene, etc.; an ether solvent such as dioxane, tetrahydrofurane, dimethoxyethane, etc.; an alcoholic solvent such as methanol, ethanol, isopropyl alcohol, etc.; and other organic solvents such as ethyl acetate, N,N-dimethylformamide, dimethylsulfoxide, acetonitrile, etc., but any other solvent can be used unless such a solvent has an undesirable effect on the reaction.

The reaction temperature is not critical. Generally, the reaction can be carried out at room temperature, on heating, on warming or under reflux.

After the reaction is completed, the product can be obtained by conventional post-treatments, but if necessary, the product may be purified by a column chromatography, recrystallization, etc.

Process 2

The starting materials for this process are represented by formula (I') having carbonate represented by $R^4OCO$ as a protecting group for the hydroxyl group of formula (I). That is, the carbonate of the compound (I') is treated under the basic condition to give a phenol compound represented by the formula (I") or an alkali metal salt thereof and the compound thus obtained is then reacted with an alkylating reagent represented by the formula (III) to prepare an oxazolidinedione compound as shown in the formula (I'''). Both the starting material (I') and the reaction intermediate (I") are novel, which are included in the compounds of this invention represented by the formula (I).

The hydrolysis of the carbonate is carried out in the presence of a base. This reaction is characterized by selectively hydrolyzing only the ester bond under the basic condition where the oxazolidinedione ring is free from hydrolysis. Examples of preferred bases which can be used include a metal carbonate such as sodium carbonate, potassium carbonate, lithium carbonate, sodium bicarbonate, potassium bicarbonate, etc.; an alkali metal hydroxide such as sodium hydroxide, potassium hydroxide, lithium hydroxide, etc.; an alkali metal alkoxide such as sodium methoxide, sodium ethoxide, lithium methoxide, etc.; and so on. The amount of base used is preferably 0.5 to 2.0 equivalent to the substrate.

The reaction is carried out in various kinds of solvents, preferably in a protic solvent such as methanol, ethanol, isopropyl alcohol, and t-butyl alcohol. Further, an aprotic solvent such as an aromatic solvent, e.g., benzene, toluene, xylene, etc.; an ether solvent, e.g., dioxane, tetrahydrofurane, dimethoxyethane, etc.; and so on can be used with a protic solvent unless such a solvent has an undesirable effect on the reaction.

The compounds of this invention (I''') can be prepared by the reaction of the oxazolidinedione compounds (I") thus obtained with the compounds represented by the formula (III).

This reaction can be carried out in the presence of various kinds of base. Examples of the bases which can be used include a basic inorganic compounds such as sodium carbonate, potassium carbonate, sodium hydroxide and potassium hydroxide; an alkali metal alkoxide such as sodium methoxide, sodium ethoxide and potassium-t-butoxide, etc.; an alkali metal hydride such as sodium hydride, potassium hydride, etc.; an alkali lithium agent such as methyl lithium, n-butyl lithium, etc.; and an alkali metal amide such as sodium amide, lithium amide, etc.

It is preferable that the reaction is carried out in an organic solvent. Examples of organic solvents which can be used include aromatic solvents such as benzene, toluene, xylene, etc.; ether solvents such as diethyl ether, dioxane, tetrahydrofurane, dimethoxyethane, etc.; ketones such as acetone, methyl ethyl ketone, etc.; nitriles such as acetonitrile, isobutyronitrile, etc.; and other organic solvents such as N,N-dimethylformamide, dimethylsulfoxide, sulfolane, etc.; and the mixture of these solvents.

In addition, when a chloride, bromide or sulfonate ester is used in this reaction among compounds represented by the formula (III), the reaction can be speeded up by the addition of iodides such as potassium iodide, sodium iodide, etc. or quaternary ammonium salts such as tetraethylammonium bromide, benzyltriethylammonium bromide, and iodide, which depends upon the compound to be reacted.

The reaction temperature differs, depending on the base and solvent used, but it is not critical, and the reaction can be carried out on cooling, at room temperature, under warming or under heating.

After the reaction is completed, the product can be obtained by conventional post-treatments, but, if necessary, it may be purified by a column chromatography, recrystallization, etc.

Furthermore, a metal salt of the phenol presented by the formula (I″) may be used in the present reaction. This metal salt can be prepared by the treatment of the compound (I′) or compound (I″) with a base, but in both cases the metal salt can be used for the next reaction without isolation from the reaction mixture.

Process 3

The compounds of this invention (I) can be prepared by hydrogenating the double bond of the compounds represented by the formula (VI) having a substituted methylidine group at the 5 position of the oxazolidinedione ring under the condition of hydrogenation.

A conventional reductive reaction of olefines can be utilized for the present reductive reaction. Heterogeneous catalysts for hydrogenation such as palladium charcoal, palladium black, palladium asbestos, palladium silica, palladium alumina, rhodium charcoal, rhodium asbestos, rhodium silica, rhodium alumina, platinum charcoal, platinum oxide, Raney nickel, etc. or homogeneous catalysts for hydrogenation comprising transition metal complexes such as palladium, rhodium, iridium, ruthenium, etc. can be used.

It is preferable that this reaction be carried out in an organic solvent. Examples of organic solvents which can be preferably used, depending upon the catalyst used, include an alcoholic solvent such as methanol, ethanol, isopropyl alcohol, ethyleneglycol, etc.; an aromatic solvent such as benzene, toluene, xylene, etc.; an ether solvent such as diethyl ether, dioxane, tetrahydrofurane, dimethoxyethane, etc.; ketones such as acetone, methyl ethyl ketone, etc.; and the mixture of these organic solvents. Especially, when a heterogeneous catalyst is used, an alcoholic solvent is preferable with respect to yield and selectivity.

The reaction time can be shortened by pressurizing the hydrogen gas in the reaction vessel to a few atmosphere though this reaction can also proceed under the atmospheric pressure of the hydrogen gas.

After the reaction is completed, the catalyst can be removed by filtration and the product can be obtained by a conventional post-treatment, but, if necessary, the product may be purified by a column chromatography, recrystallization, etc.

The processes for preparing the starting materials are explained below in detail.

Process for Preparing the Starting Compounds 1

The carbamate compounds represented by the formula (II) can be prepared by the reaction of an arylisocyanate represented by the formula (V) with α-hydroxycarboxylate represented by the formula (VI).

This reaction is generally carried out in the presence of a base. Examples of preferred bases which can be used include a tertiary amine such as triethylamine, tripropylamine, tributylamine, N-methylmorphorine, etc.; an aromatic amine such as pyridine, lutidine, etc.; and an alkali metal inorganic compound such as sodium carbonate, potassium carbonate, etc.

This reaction is carried out in an organic solvent. Examples of preferred organic solvents which can be used include an aromatic solvent such as benzene, toluene, xylene, etc.; an ether solvent such as diethyl ether, dioxane, tetrahydrofurane, dimethoxyethane, etc.; and other organic solvents such as ethyl acetate, N,N-dimethylformamide, dimethylsulfoxide, acetonitrile, etc., but any other organic solvent can be used unless such a solvent has an undesirable effect on the reaction.

The reaction temperature is not critical, and generally the reaction is carried out at room temperature, under warming, under heating or under reflux.

After the reaction is completed, the product can be obtained by the conventional post-treatments but, if necessary, it may be purified by a column chromatography, recrystallization, etc.

Process for Preparing the Starting Compounds 2

The carbamate compounds represented by the formula (II) can be prepared by hydrogenating the double bond of the carbamate compounds having a double bond in their molecules represented by the formula (VII), which are known compounds as described in Japanese Patent Public Disclosure No. 62-174065 corresponding to U.S. Pat. No. 4,818,272.

A conventional reductive reaction of olefines can be utilized for the present reductive reaction. Heterogeneous catalysts for hydrogenation such as palladium charcoal, palladium black, palladium asbestos, palladium silica, palladium alumina, rhodium charcoal, rhodium asbestos, rhodium silica, rhodium alumina, platinum charcoal, platinum oxide, Raney nickel, etc. or homogeneous catalysts for hydrogenation comprising transition metal complexes such as palladium, rhodium, iridium, ruthenium, etc. can be used.

It is preferable that this reaction be carried out in an organic solvent. Examples of organic solvents which can be preferably used, depending upon the catalyst used, include an alcoholic solvent such as methanol, ethanol, isopropyl alcohol, etc.; an aromatic solvent such as benzene, toluene, xylene, etc.; an ether solvent such as diethyl ether, dioxane, tetrahydrofurane, dimethoxyethane, etc.; ketones such as acetone, methyl ethyl ketone, etc.; and the mixture of these organic solvents. Especially, when a heterogeneous catalyst is used, an alcoholic solvent is preferable with respect to yield and selectivity.

The reaction time can be shortened by pressurizing the hydrogen gas in the reaction vessel to a few atmosphere though this reaction can also proceed under the atmospheric pressure of the hydrogen gas.

After the reaction is completed, the catalyst can be removed by filtration and the product can be obtained by the conventional post-treatment, but, if necessary, the product may be purified by a column chromatography, recrystallization, etc.

Typical examples of the oxazolidinedione compounds represented by the formula (I) which can be synthesized according to the present invention are shown in Table 1.

TABLE 1
Oxazolidinedione compounds

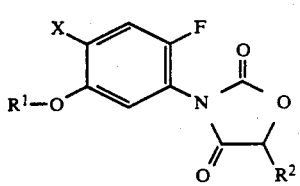

| Compound No. | Example No. | X | R¹ | R² |
|---|---|---|---|---|
| 1 | 1, 2 | Cl | $(CH_3)_2CH$ | $(CH_3)_2CH$ |
| 2 | 3 | Cl | cyclo-$C_5H_9$ | $(CH_3)_2CH$ |
| 3 | 4 | Cl | $HC\equiv CCH_2$ | $(CH_3)_2CH$ |
| 4 | 5 | Cl | $(CH_3)_2CH$ | $CH_3CH_2CH$<br>      $\|$<br>     $CH_3$ |
| 5 | 6 | Cl | $(CH_3)_2CH$ | cyclo-$C_5H_9$ |
| 6 | 7 | Cl | $CH_3CH_2$ | $(CH_3)_2CH$ |
| 7 | 8, 9 | Cl | $H_2C=CHCH_2$ | $(CH_3)_2CH$ |
| 8 | 10 | Cl | $H_2C=CCH_2$<br>      $\|$<br>     $CH_3$ | $(CH_3)_2CH$ |
| 9 | 11 | F | $HC\equiv CCH_2$ | $(CH_3)_2CH$ |
| 10 | 12 | Cl | $CH_3CH_2CH_2$ | $(CH_3)_2CH$ |
| 11 | 13 | Cl | H | $(CH_3)_2CH$ |
| 12 | 14, 15 | Cl | $CH_3OCO$ | $(CH_3)_2CH$ |

The present invention is described in detail below with reference to examples, preparation examples and experimental examples.

EXAMPLE 1

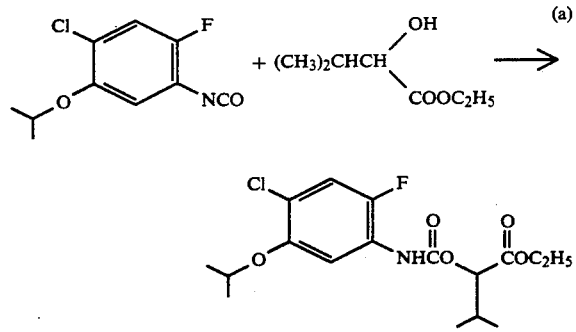

A small amount of propylene oxide and triethylamine (0.2 ml) were added to a solution of 2-fluoro-4-chloro-5-isopropoxyphenylisocyanate (500 mg, 2.18 mmol) and ethyl 2-hydroxyisovalerate (476 mg, 3.26 mmol) in ether (30 ml), and the mixture was stirred at room temperature for 2 hours. After completion of the reaction, the solution was washed with 1N hydrochloric acid three times and then the organic layer was dried and concentrated under reduced pressure. The resulting pale brown oil was purified by silica gel column chromatography (eluent: ethyl acetate/hexane=1/10) to give a pure product of ethyl 2-{N-(2'-fluoro-4'-chloro-5'-isopropoxyphenyl)carbamoyloxy}isovalerate (550 mg, yield 67%).

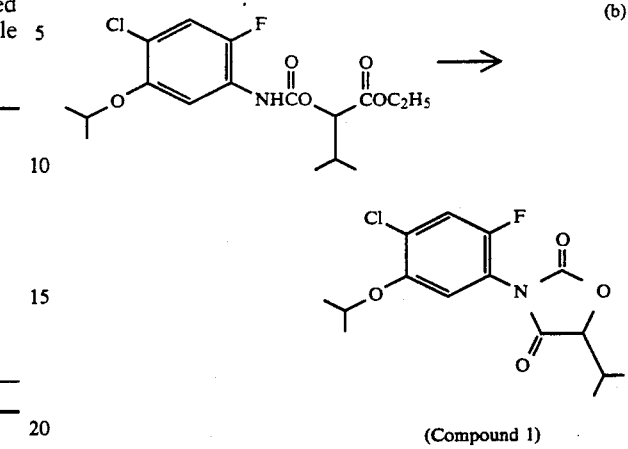

A catalytic amount of sodium acetate was added to a solution of ethyl 2-{N-(2'-fluoro-4'-chloro-5'-isopropoxyphenyl)carbamoyloxy}isovalerate (500 mg, 1.33 mmol) in toluene (30 ml) and the mixture was stirred for 5 hours under reflux. After completion of the reaction, the solution was washed with 1N hydrochloric acid. The organic layer was dried and then the solvent was distilled off under reduced pressure. The resulting oily product was purified by silica gel column chromatography (eluent: ethyl acetate/hexane=1/10) to give a pure product of 3-(2'-fluoro-4'-chloro-5'-isopropoxyphenyl)-5-isopropyl-1,3-oxazolidine-2,4-dione [Compound 1] (240 mg, yield 55%).

EXAMPLE 2

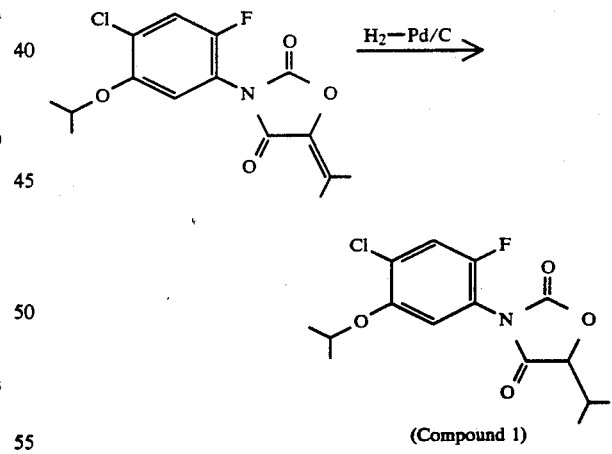

A catalytic amount of 10% Pd/C (80 mg) was added to a solution of 3-(2'-fluoro-4'-chloro-5'-isopropoxyphenyl)-5-isopropyliden-1,3-oxazolidine-2,4-dione (400 mg, 1.22 mmol) in ethanol (30 ml) and the reaction was carried out at room temperature under a hydrogen atmosphere at normal pressure until the absorption of hydrogen gas was completed. After completion of the reaction, the catalyst was filtered off and the resulting filtrate was concentrated under reduced pressure to give a colorless and transparent oily product. The product was purified by silica gel column chromatography (eluent: ethyl acetate/hexane=1/10) to give a pure white crystal of 3-(2'-fluoro-4'-chloro-5'-isopropoxyphenyl)-5-isopropyl-1,3-oxazolidine-2,4-dione [Compound 1] (310 mg, yield 77%).

EXAMPLE 3

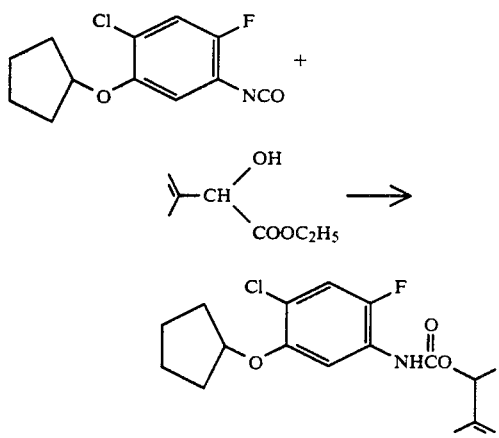

A small amount of propylene oxide and triethyl amine (0.2 ml) were added to a solution of 2-fluoro-4-chloro-5-cyclopentyloxyphenylisocyanate (800 mg, 3.13 mmol) and ethyl 2-hydroxy-3-methyl-3-butenoate (679 mg, 4.71 mmol) in ether (30 ml) and the mixture was stirred at room temperature for 2 hours. After completion of the reaction, the solution was washed with 1N hydrochloric acid three times and then the organic layer was dried and concentrated under reduced pressure. The resulting pale brown oil was purified by silica gel column chromatography (eluent: ethyl acetate/hexane=1/10) followed by recrystallization from ether-hexane to give a pure product of ethyl 2-{N-(2'-fluoro-4'-chloro-5'-cyclopentyloxyphenyl)carbamoyloxy}-3-methyl-3-butenoate (1.01 g, yield 81%).

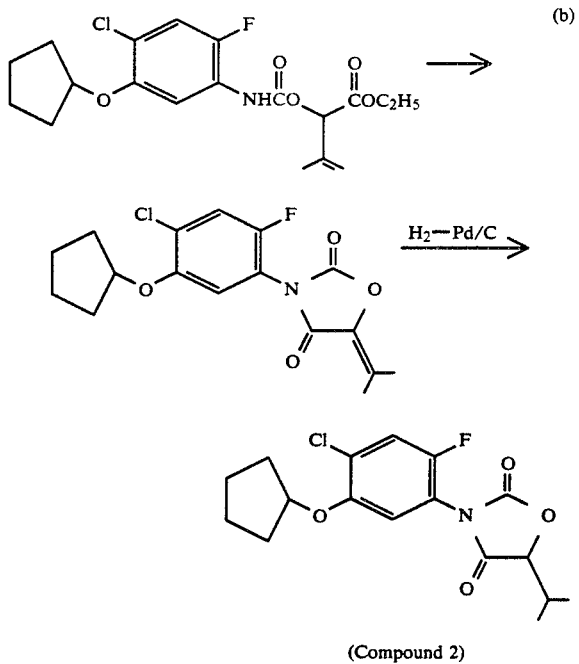

(Compound 2)

A catalytic amount of sodium acetate was added to a solution of ethyl 2-{N-(2'-fluoro-4'-chloro-5'-cyclopentyloxyphenyl)carbamoyloxy}-3-methyl-3-butenoate (800 mg, 2.0 mmol) in toluene (30 ml) and the mixture was stirred for 3 hours under reflux. After completion of the reaction, the solution was washed with 1N hydrochloric acid. The organic layer was dried and then the solvent was distilled off under reduced pressure. The resulting oily product was purified by silica gel column chromatography (eluent: ethyl acetate/hexane=1/5) to give a pure white solid of 3-(2'-fluoro-4'-chloro-5'-cyclopentyloxyphenyl)-5-isopropyliden-1,3-oxazolidine-2,4-dione (540 mg, yield 76%). $^1$H—NMR (CDCl$_3$, TMS, δ ppm): 1.58–1.91 (8H,m), 2.00 (3H,s), 2.26 (3H,s), 4.73 (1H,m), 6.77 (1H,d), 7.27 (1H,d). IR (KBr disk, cm$^{-1}$): 1820, 1743, 1693. MP: 98°–99.5° C.

A catalytic amount of 10% Pd/C (100 mg) was added to a solution of 3-(2'-fluoro-4'-chloro-5'-cyclopentyloxyphenyl)-5-isopropyliden-1,3-oxazolidine-2,4-dione obtained above (50 mg, 1.41 mmol) in ethanol (30 ml). The reaction was carried out at room temperature under a hydrogen atmosphere at normal pressure until the absorption of hydrogen gas was completed. After completion of the reaction, the catalyst was filtered off and the resulting filtrate was concentrated under reduced pressure to give a colorless and transparent oily product. A small amount of methanol was added to the oily product and the mixture was allowed to cool to give a white crystal (360 mg, yield 72%). The product thus obtained was confirmed to be 3-(2'-fluoro-4'-chloro-5'-cyclopentyloxyphenyl)-5-isopropyl-1,3-oxazolidine-2,4-dione [Compound 2] from the analytical data of spectra and others.

EXAMPLE 4

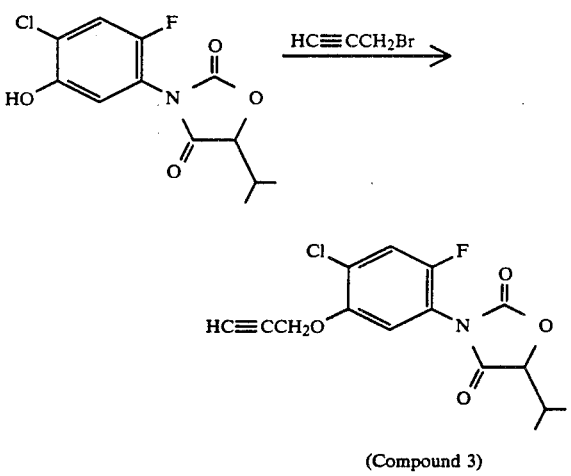

(Compound 3)

Potassium carbonate (340 mg) was added to a solution of 3-(2'-fluoro-4'-chloro-5'-hydroxyphenyl)-5-isopropyl-1,3-oxazolidine-2,4-dione (700 mg, 2.43 mmol) in acetonitrile (30 ml) and the mixture was stirred for 1 hour under reflux. After the addition of propargyl bromide (2 ml), the resulting mixture was stirred for an additional 3 hours under reflux. After completion of the reaction, the solvent was distilled under reduced pressure. Then 1N hydrochloric acid was added and the mixture was extracted with ether. After drying the ether layer, the solvent was distilled under reduced pressure to give a pale yellow oily product. The product was purified by silica gel column chromatography (eluent: ethyl acetate/hexane=1/10) to give a pure product of 3-(2'-fluoro-4'-chloro-5'-propargyloxyphenyl)-5-isopropyl-1,3-oxazolidine-2,4-dione [Compound 3] (480 mg, yield 61%).

EXAMPLE 5

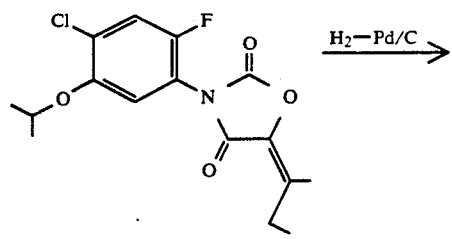

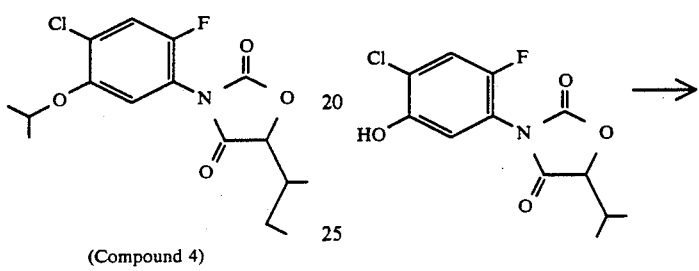

(Compound 4)

A catalytic amount of 10% Pd/C (60 mg) was added to a solution of 3-(2'-fluoro-4'-chloro-5'-isopropoxyphenyl)-5-(2''-butyliden)-1,3-oxazolidine-2,4-dione (300 mg, 0.88 mmol) in ethanol (30 ml) and the reaction was carried out at room temperature under a hydrogen atmosphere at normal pressure until the absorption of hydrogen gas was completed. After completion of the reaction, the catalyst was filtered off and the resulting filtrate was concentrated under reduced pressure to give a colorless and transparent oily product. The product was purified by silica gel column chromatography (eluent: ethyl acetate/hexane=1/10) to give a pure white crystal of 3-(2'-fluoro-4'-chloro-5'-isopropoxyphenyl)-5-(2''-butyl)-1,3-oxazolidine-2,4-dione [Compound 4] (240 mg, yield 80%).

EXAMPLE 6

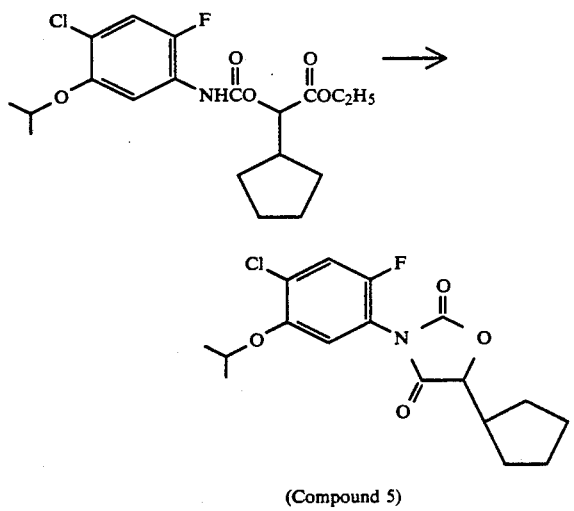

(Compound 5)

A catalytic amount of sodium acetate was added to a solution of methyl 2-{N-(2'-fluoro-4'-chloro-5'-isopropoxyphenyl)carbamoyloxy}-2-cyclopentylacetate (400 mg, 1.0 mmol) in N,N-dimethylformamide (30 ml) and the mixture was stirred at 50° C. for 8 hours. After completion of the reaction, 1N hydrochloric acid was added and the mixture was extracted with ether. The ether layer was washed with 1N hydrochloric acid three times, dried and concentrated under reduced pressure to give a oily product. The product was purified by silica gel column chromatography (eluent: ethyl acetate/hexane=1/10) and recrystallized from methanol to give a pure product of 3-(2'-fluoro-4'-chloro-5'-isopropoxyphenyl)-5-cyclopentyl-1,3-oxazolidine-2,4-dione [Compound 5] (170 mg, yield 48%).

EXAMPLE 7

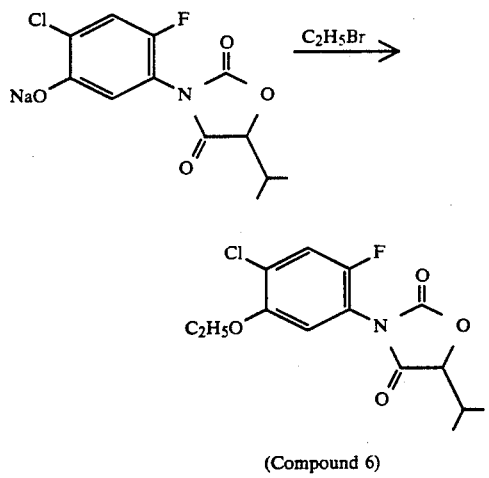

(Compound 6)

Tetrahydrofuran (30 ml) was added to oily (ca. 60%) sodium hydride (170 mg, 25 mmol) which had been washed with hexane. To the mixture was added 3-(2'-fluoro-4'-chloro-5'-hydroxyphenyl)-5-isopropyl-1,3-oxazolidine-2,4-dione (1.0 g, 3.48 mmol), and the resulting mixture was stirred at room temperature until the generation of hydrogen gas ceased. The solvent was removed to give a white solid of 3-(2'-fluoro-4'-chloro-5'-sodiumoxyphenyl)-5-isopropyl-1,3-oxazolidine-2,4-dione. The solid was dissolved in acetonitrile (30 ml) and ethyl iodide (2 ml) was added to the solution. The mixture was stirred for 3 hours under reflux. After completion of the reaction, 1N hydrochloric acid was added and the product was extracted with chloroform. After drying the organic layer, the solvent was distilled under reduced pressure to give a pale yellow oily product. The product was recrystallized from methanol to give 3-(2'-fluoro-4'-chloro-5'-ethoxyphenyl)-5-isopropyl-1,3-oxazolidine-2,4-dione [Compound 6] (700 mg, yield 64%).

EXAMPLE 8

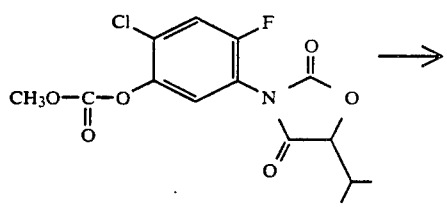

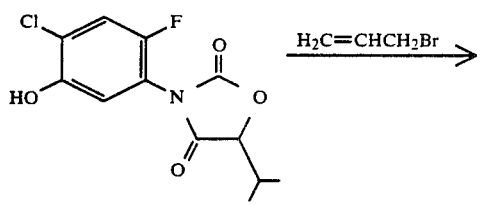

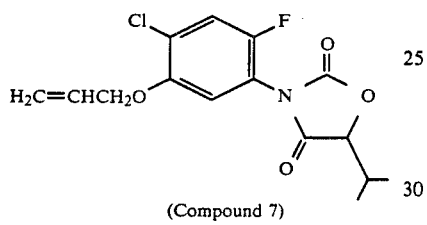

(Compound 7)

Potassium carbonate (3.04 g, 22.0 mmol) was added to a solution of 3-(2'-fluoro-4'-chloro-5'-methoxycarbonyloxyphenyl)-5-isopropyl-1,3-oxazolidine-2,4-dione (15.2 mg, 44.0 mmol) in dry methanol (150 ml) and the mixture was stirred at room temperature for 3 hours. After completion of the reaction, a saturated aqueous solution of ammonium chloride was added and the product was extracted with ether. The ether layer was dried and the solvent was then distilled under reduced pressure to give a pale yellow oily product. The product was purified by silica gel column chromatography (eluent: ethyl acetate/hexane × ⅓) to give 3-(2'-fluoro-4'-chloro-5'-hydroxyphenyl)-5-isopropyl-1,3-oxazolidine-2,4-dione (10.5 g, yield 83%). The phenol derivative thus obtained (700 mg, 2.43 mmol) was dissolved in acetonitrile (30 ml). To the solution was added aryl bromide (2 ml) and potassium carbonate (340 mg) and the mixture was stirred for 3 hours under reflux. After completion of the reaction, the solvent was distilled under reduced pressure. After addition of 1N hydrochloric acid, the product was extracted with ether. The organic layer was dried and the solvent was distilled under reduced pressure to give a pale yellow oily product. The product was purified by silica gel column chromatography (eluent: ethyl acetate/hexane × 1/10) to give a pure product of 3-(2'-fluoro-4'-chloro-5'aryloxyphenyl)-5-isopropyl-1,3-oxazolidine-2,4-dione [Compound 7] (540 mg, yield 68%).

EXAMPLE 9

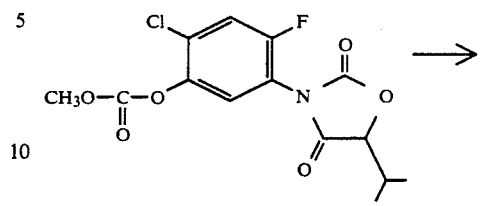

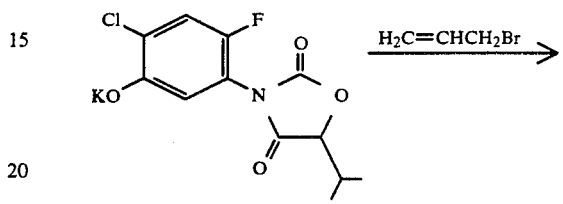

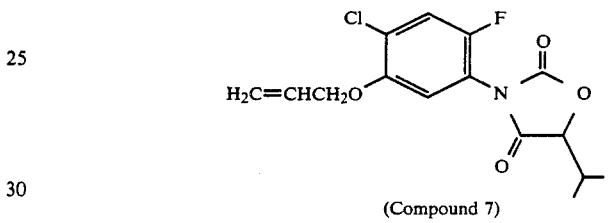

(Compound 7)

Potassium carbonate (160 mg, 1.16 mmol) was added to a solution of 3-(2'-fluoro-4'-chloro-5'-methoxycarbonyloxyphenyl)-5-isopropyl-1,3-oxazolidine-2,4-dione (800 mg, 2.31 mmol) in dry methanol (30 ml) and the mixture was stirred at room temperature for 2 hours. After the solvent was distilled under reduced pressure, acetonitrile (30 ml) and aryl bromide (2 ml) were added to the resulting residue and the resulting mixture was then stirred for 3 hours. After completion of the reaction, the solvent was distilled under reduced pressure and 1N hydrochloric acid was added. The product was extracted with ether and the ether layer was dried. The solvent was distilled under reduced pressure to give a pale yellow oily product. The product was purified by silica gel column chromatography (eluent: ethyl acetate/hexane=1/10) to give 3-(2'-fluoro-4'-chloro-5'-aryloxyphenyl)-5-isopropyl-1,3-oxazolidine-2,4-dione [Compound 7] (240 mg, yield 32%).

EXAMPLE 10

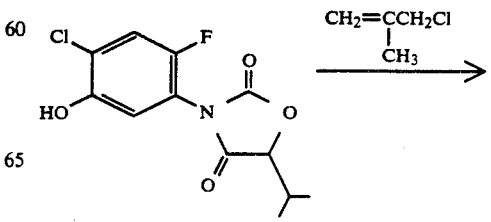

17

-continued

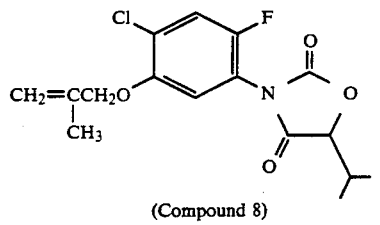

(Compound 8)

Potassium carbonate (340 mg) was added to a solution of 3-(2'-fluoro-4'-chloro-5'-isopropyl-1,3-oxazolidine-2,4dione (700 mg, 2.43 mmol) in N,N-dimethylformamide (30 ml) and the mixture was stirred at 70° C. for 40 minutes. After addition of methallyl chloride (2.0 ml), the resulting mixture was stirred at 70° C. for an additional 12 hours. After completion of the reaction, 1N hydrochloric acid was added and the mixture was extracted with ether. The ether layer was washed with 1N hydrochloric acid three times. After dryer the ether layer, the solvent was distilled under reduced pressure to give a pale yellow oily product. The product was purified by silica gel column chromatography (eluent: ethyl acetate/hexane=1/10) to give a pure colorless and transparent oily product of 3-(2'-fluoro-4'-chloro-5'-methallyloxyphenyl)-5-isopropyl-1,3-oxazolidine-2,4-dione [Compound 8] (480 mg, yield 58%).

EXAMPLE 11

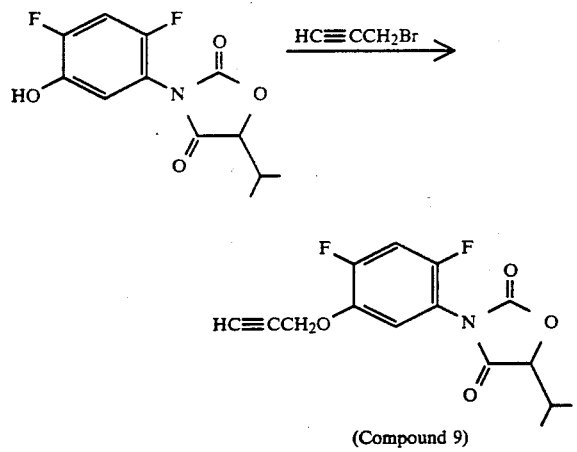

(Compound 9)

3-(2', 4'-difluoro-5'-hydroxyphenyl)-5-isopropyl-1,3-oxazolidine-2,4-dione (878 mg, 3.25 mmol) was reacted with propargyl bromide in a manner similar to that of Example 4 to give 3-(2',4'-difluoro-5'-propargyloxyphenyl)-5-isopropyl-1,3-oxazolidine-2,4-dione [Compound 9] (503 mg, yield 52%).

EXAMPLE 12

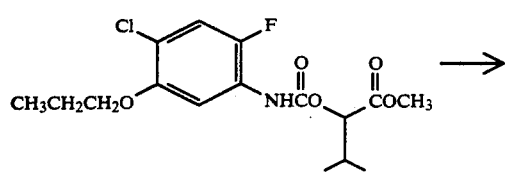

18

-continued

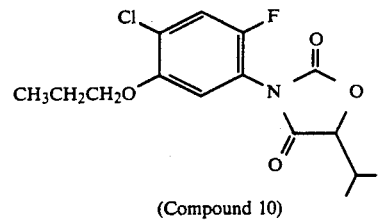

(Compound 10)

Methyl 2-{N-(2'-fluoro-4'-chloro-5'-propoxyphenyl)-carbamoyloxy}isovalerate was prepared by reacting 2-fluoro-4-chloro-5-propoxyphenylisocyanate and methyl 2-hydroxyisovalarate. In a manner similar to that of Example 1, potassium carbonate (50 mg) was added to a solution of the methyl ester (362 mg, 1.0 mmol) in acetonitrile (30 ml) and the mixture was stirred at room temperature for 6 hours. The reaction mixture was then treated in a manner similar to that of Example 1 to give 3-(2'-fluoro-4'-chloro-5'-propoxyphenyl)-5-isopropyl-1,3-oxazolidine-2,4-dione [Compound 10] (205 mg. yield 62%).

EXAMPLE 13

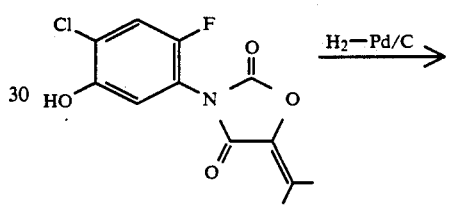

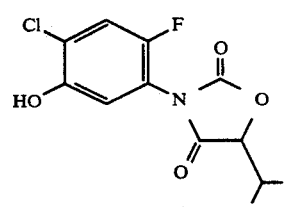

(Compound 11)

A catalytic amount of 10% Pd/C (40 mg) was added to a solution of 3-(2'-fluoro-4'-chloro-5'-hydroxyphenyl)-5-isopropyliden-1,3-oxazolidine-2,4-dione (200 mg, 0.70 mmol) in ethanol (20 ml) and reaction was carried out at room temperature under a hydrogen atmosphere at normal pressure until the absorption of hydrogen gas was completed. After completion of the reaction, the catalyst was filtered off and the resulting filtrate was concentrated under reduced pressure to give a colorless and transparent oily product. The product was purified by silica gel column chromatography (eluent: ethyl acetate/hexane=1/10) to give a pure white crystal of 3-(2'-fluoro-4'-chloro-5'-hydroxyphenyl)-5-isopropyl-1,3-oxazolidine-2,4-dione [Compound 11] (180 mg, yield 89%).

EXAMPLE 14

(a)

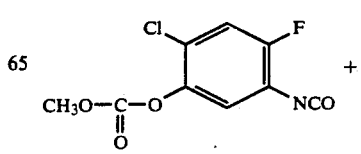

-continued

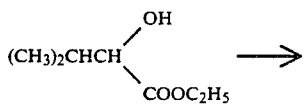

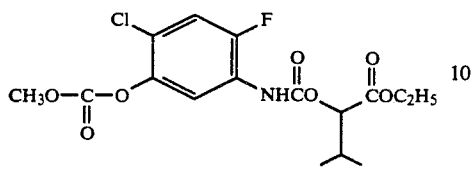

Propylene oxide (3 ml) and triethyl amine (2.0 ml) were added to a solution of 2-fluoro-4-chloro-5-methoxycarbonyloxyphenylisocyanate (25 g, 102 mmol) and ethyl 2-hydroxyisovalerate (22.4 g, 153 mmol) in ether (300 ml) and the mixture was stirred at room temperature for 3 hours. After completion of the reaction, the solution was washed with 1N hydrochloric acid three times and then the organic layer was dried and concentrated under reduced pressure. The resulting oil was purified by silica gel column chromatography (eluent: ethyl acetate/hexane=⅓) to give ethyl 2-{N-(2'-fluoro-4'-chloro-5'-methoxycarbonyloxyphenyl)carbamoyloxy}isovalerate (24.5 g, yield 61%). MP: 79°–81° C.

(b)

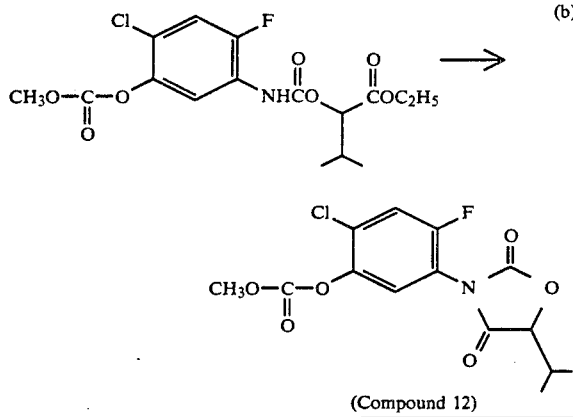

(Compound 12)

A catalytic amount of sodium acetate was added to a solution of ethyl 2-{N-(2'-fluoro-4'-chloro-5'-methoxycarbonyloxyphenyl)carbamoyloxy}isovalerate (24.5 g, 62.5 mmol) in toluene (200 ml) and the mixture was stirred for 3 hours under reflux. After completion of the reaction, 1N hydrochloric acid was added to the solution and the product was extracted with ether. The organic layer was washed with 1N hydrochloric acid three times, dried and concentrated under reduced pressure. The resulting oily product was purified by silica gel column chromatography (eluent: ethyl acetate/hexane=⅓) to give 3-(2'-fluoro-4'-chloro-5'-methoxycarbonyloxyphenyl)-5-isopropyl-1,3-oxazolidine-2,4-dione [Compound 12] (15.0 g, yield 70%).

EXAMPLE 15

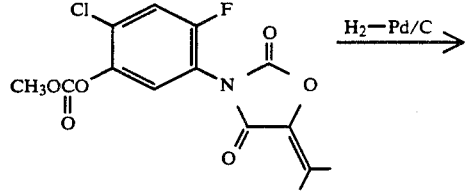

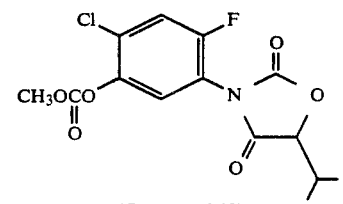

(Compound 12)

A catalytic amount of 10% Pd/C (80 mg) was added to a solution of 3-(2'-fluoro-4'-chloro-5'-methoxycarbonyloxyphenyl)-5-isopropyliden-1,3-oxazolidine-2,4-dione (370 mg, 1.08 mmol) in ethanol (30 ml) and the reaction was carried out at room temperature under a hydrogen atmosphere at normal pressure until the absorption of hydrogen gas was completed. After completion of the reaction, the catalyst was filtered off and the resulting filtrate was concentrated under reduced pressure to give a colorless and transparent oily product. The product was purified by silica gel column chromatography (eluent: ethyl acetate/hexane=1/10) to give a pure product of 3-(2'-fluoro-4'-chloro-5'-methoxycarbonyloxyphenyl)-5-isopropyl-1,3-oxazolidine-2,4-dione [Compound 12] (350 mg, yield 94%).

TABLE 2

| Compound No. | Melting point (°C.) | Empirical formula | C (%) Found | C (%) Calc'd | H (%) Found | H (%) Calc'd | N (%) Found | N (%) Calc'd |
|---|---|---|---|---|---|---|---|---|
| 1 | 67–68 | $C_{15}H_{17}ClFNO_4$ | 54.92 | 54.64 | 5.27 | 5.20 | 4.22 | 4.25 |
| 2 | glassy oil | $C_{17}H_{19}ClFNO_4$ | 57.71 | 57.39 | 5.90 | 5.38 | 4.04 | 3.94 |
| 3 | glassy oil | $C_{15}H_{13}ClFNO_4$ | 54.86 | 55.31 | 4.16 | 4.02 | 4.03 | 4.30 |
| 4 | glassy oil | $C_{16}H_{19}ClFNO_4$ | 55.83 | 55.90 | 5.78 | 5.57 | 3.77 | 4.07 |
| 5 | 71–72.5 | $C_{17}H_{19}ClFNO_4$ | 57.23 | 57.39 | 5.45 | 5.38 | 3.83 | 3.94 |
| 6 | 60.5–61.5 | $C_{14}H_{15}ClFNO_4$ | 53.20 | 53.26 | 4.87 | 4.79 | 4.34 | 4.44 |
| 7 | glassy oil | $C_{15}H_{15}ClFNO_4$ | 54.69 | 54.97 | 4.87 | 4.61 | 3.99 | 4.27 |
| 8 | 59.5–61 | $C_{16}H_{17}ClFNO_4$ | 56.47 | 56.23 | 5.09 | 5.01 | 4.06 | 4.10 |
| 9 | 80–83 | $C_{15}H_{13}F_2NO_4 \cdot \tfrac{1}{2}H_2O$ | 56.80 | 56.07 | 4.38 | 4.49 | 4.73 | 4.36 |
| 10 | oil | $C_{13}H_{13}ClFNO_4$ | 51.81 | 51.75 | 5.45 | 4.35 | 4.36 | 4.64 |
| 11 | 99–100 | $C_{12}H_{11}ClFNO_4$ | 50.02 | 50.10 | 3.97 | 3.85 | 4.64 | 4.87 |
| 12 | 83–87 | $C_{14}H_{13}ClFNO_6$ | 48.47 | 48.64 | 3.93 | 3.79 | 4.01 | 4.05 |

TABLE 3

| Compound No. | $^1$H-NMR Spectrum (CDCl$_3$, TMS, δ ppm) | IR Spectrum (cm$^{-1}$) |
|---|---|---|
| 1 | 7.28(1H, d), 6.86(1H, d), 4.79(1H, d), 4.43(1H, sep), 2.15–2.60(1H, m), 1.33(6H, d), 1.14(3H, d), 1.05(3H, d) | 1820 1750 |
| 2 | 7.25(1H, d), 6.76(1H, d), 4.79(1H, d), 4.60–4.90(1H, m), 2.10–2.60(1H, m), | 1830 1755 |

TABLE 3-continued

| Compound No. | $^1$H-NMR Spectrum (CDCl$_3$, TMS, δ ppm) | IR Spectrum (cm$^{-1}$) |
|---|---|---|
|  | 1.40-2.10(8H, br), 1.15(3H, d), 1.06(3H, d) |  |
| 3 | 7.30(1H, d), 7.00(1H, d), 4.82(1H, d), 4.72(2H, d), 2.16-2.63(1H, m), 2.56(1H, t), 1.17(3H, d), 1.07(3H, d) | 1828 1752 |
| 4 | 7.22(1H, d), 6.78(1H, d), 4.92, 4.83(total 1H, each d), 4.40(1H, sep), 1.82-2.29(1H, m), 1.34(6H, d), 0.72-1.82(8H, m) | 1828 1755 |
| 5 | 7.18(1H, d), 6.83(1H, d), 4.92(1H, d), 4.43(1H, sep), 2.26-2.74(1H, m), 1.43-2.10(8H, br), 1.35(6H, d) | 1820 1755 |
| 6 | 7.28(1H, d), 6.77(1H, d), 4.78(1H, d), 4.03(2H, q), 2.10-2.58(1H, m), 1.43(3H, t), 1.16(3H, d), 1.06(3H, d) | 1830 1758 |
| 7 | 7.27(1H, d), 6.79(1H, d), 5.79-6.25(1H, m), 5.20-5.59(2H, m), 4.78(1H, d), 4.54(2H, d), 2.10-2.53(1H, m), 1.16(3H, d), 1.06(3H, d) | 1832 1758 |
| 8 | 7.30(1H, d), 6.81(1H, d), 5.11(1H, s), 5.01(1H, s), 4.80(1H, d), 4.44(2H, s), 2.19-2.58(1H, m), 1.82(3H, s), 1.16(3H, d), 1.07(3H, d) | 1832 1757 |
| 9 | 7.04(1H, t), 6.95(1H, t), 4.87(1H, d), 4.75(2H, d), 2.60(1H, t), 2.12-2.60(1H, m), 1.14(6H, dd) | 1815 1750 |
| 10 | 7.35(1H, d), 6.85(1H, d), 4.86(1H, d), 3.98(2H, t), 2.28-2.62(1H, m), 1.61-2.10 (2H, m), 1.20(3H, t), 1.02-1.32(6H, m) | 1820 1750 |
| 11 | 7.21(1H, d), 6.97(1H, d), 6.46(1H, br), 4.83(1H, d), 2.10-2.56(1H, m), 1.16(3H, d), 1.06(3H, d) | 1828 1755 |
| 12 | 7.42(1H, d), 7.30(1H, d), 4.85(1H, d), 3.94(3H, s), 2.13-2.63(1H, m), 1.18(3H, d), 1.08(3H, d) | 1835 1773 1755 |

The novel oxazolidinedione compounds of the present invention thus obtained have an excellent herbicidal activity as described above.

In using the oxazolidinedione compounds of this invention as herbicidal agents, the compounds per se can be used, but generally they are preferably used in the form of a herbicidal composition in admixture with one or more auxiliary agents. Examples of the auxiliary agent which can be used includes various carriers, vulcanizing agents, solvents, surface active agents, stabilizers and the like. The compounds of the present invention are preferably used by blending with these auxiliary agent in a conventional form of herbicidal compositions such as wettable powders, emulsions, powders or dust, granules, etc.

Examples of the solvent which can be suitably used as an auxiliary agent in the herbicidal composition of this invention include, for example, water, alcohols, ketones, ethers, aliphatic and aromatic hydrocarbons, halogenated hydrocarbons, acid amides, esters, nitriles, or a mixture of these solvents. Examples of the vulcanizing agents which can be used in the herbicidal composition include mineral powders, for example, clays such as kaolin or bentonite, talcs such as talc or pyrophyllite, oxides such as diatomaceous earth or white carbon, and vegetable powders such as soybean powder, carboxymethyl cellulose, etc. Also, surface active agents can be used in the herbicidal composition of this invention as a spreading agent, a dispersing agent, an emulsifying agent or a penetrating agent. Examples of the surface active agents include non-ionic surface active agents, cationic surface active agents and amphoteric surface active agents. These surface active agents can be used alone or as a mixture of two or more agents depending upon the purpose of use.

A herbicidal composition of this invention containing the oxazolidinedione compound can be used for soil treatment, water surface treatment, the stalk and leaves treatment, and the like, and exhibits a particularly excellent herbicidal activity when it is applied during the period before or just after the germination of the weeds to be killed.

The herbicidal composition containing the oxazolidinedione of this invention as an active ingredient can also contain other active agents which do not adversely affect the herbicidal activity of the oxazolidinedione compounds of this invention, for example, herbicides, insecticides, fungicides, plant growth regulators and the like, or can be used in combination with these active agents.

Examples of herbicidal compositions of this invention as an active component, and the herbicidal effects of these compositions are shown in detail in the following examples. Unless otherwise indicated, all parts are by weight.

PREPARATION EXAMPLE 1

Emulsion

Twenty parts of Compound 1, 35 parts of xylene, 40 parts of cyclohexanone and 5 parts of Solbol 90A ® (Toho Chemical Co., Ltd.) were uniformly mixed to form an emulsion. An emulsion was also prepared in the same manner using one of Compounds 2-12 instead of Compound 1 used above.

PREPARATION EXAMPLE 2

Wettable Powder

Fifty parts of Compound 1, 25 parts of diatomaceous earth, 22 parts of clay and 3 parts of Lunox R 100C ® (Toho Chemical Co., Ltd.) was mixed and milled uniformly, and a predetermined amount of water was added to the resulting mixture to form a wettable powder. A wettable powder was also prepared in the same manner using one of Compounds 2-12 instead of Compound 1 used above.

PREPARATION EXAMPLE 3

Granules

Five parts of Compound 1, 35 parts of bentonite, 55 parts of talc and 5 parts of sodium ligninsulfonate was mixed and milled uniformly, and water was added thereto. The resulting mixture was thoroughly kneaded, extruded from a granulator, and the resulting granules were dried and subjected to a treatment for regulating the grain size to form desired granules. A granule was also prepared in the same manner using one of Compounds 2-12 instead of Compound 1 used above.

EXPERIMENTAL EXAMPLE 1

Herbicidal Effect on Weeds in Paddy Field

Paddy field soil was placed in Wagnel pots of 1/5000 Are, and seeds of *Echinochloa Crus-galli, Monochoria vaginalis* and *Ammania multiflora* were sown, and seedings of the rice plant ("Nihombare" species) of a 2-3 leaf time were also transplanted in the pots. The pots were kept under wet conditions. After 5 days, the surface of the pots was submerged to a water depth of 4 cm, and the water surface was treated with predetermined amounts of a diluted emulsion prepared in accordance with Preparation Example 1 or a diluted solution of the wettable powder prepared in accordance with Preparation Example 2 in a amount of 20 g, 10 g or 5 g of Compounds 1-10 and Control Compounds 1-3 listed below per Are. On the 20th day after this treatment, both the herbicidal effect on the test weeds and the phytotoxicity to the rice plant were evaluated according to the following rating. The results obtained are shown in Table 4.

| | Evaluation Rating | |
|---|---|---|
| Herbicidal activity | Proportion of weeds (%) | Phytotoxicity |
| 0 | 81-100 | — no damage |
| 1 | 61-80 | + slight damage |
| 2 | 41-60 | ++ small damage |
| 3 | 21-40 | +++ medium damage |
| 4 | 6-20 | ++++ heavy damage |
| 5 | 0-5 | x dead |

Control Compound 1

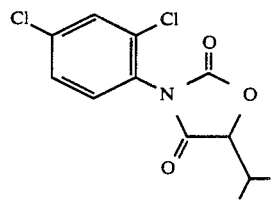

Control Compound 2

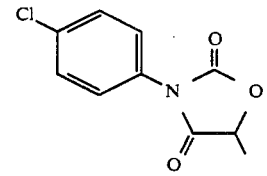

Control Compound 3 (MO)

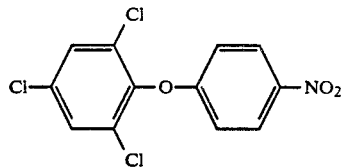

TABLE 4

| Test compound | Amount applied (g/Are) | Degree of herbicidal effect | | | Phytotoxicity to rice plant |
|---|---|---|---|---|---|
| | | E. Crusgalli | M. vaginalis | A. multiflora | |
| 1 | 10 | 5 | 5 | 5 | — |
| | 3 | 5 | 5 | 5 | — |
| | 1 | 5 | 5 | 5 | — |
| 2 | 10 | 5 | 5 | 5 | — |
| | 3 | 5 | 5 | 5 | — |
| | 1 | 4 | 5 | 5 | — |
| 3 | 10 | 5 | 5 | 5 | — |
| | 3 | 5 | 5 | 5 | + |
| | 1 | 3 | 5 | 5 | — |
| 4 | 10 | 5 | 5 | 5 | + |
| | 3 | 4 | 5 | 5 | — |
| | 1 | 3 | 5 | 5 | — |
| 5 | 10 | 5 | 5 | 5 | + |
| | 3 | 5 | 5 | 5 | — |
| | 1 | 4 | 5 | 5 | — |
| 6 | 10 | 5 | 5 | 5 | + |
| | 3 | 5 | 5 | 5 | — |
| | 1 | 4 | 5 | 5 | — |
| 7 | 10 | 5 | 5 | 5 | — |
| | 3 | 5 | 5 | 5 | + |
| | 1 | 3 | 5 | 5 | — |
| 8 | 10 | 5 | 5 | 5 | + |
| | 3 | 5 | 5 | 5 | — |
| | 1 | 5 | 5 | 5 | — |
| 9 | 10 | 5 | 5 | 5 | + |
| | 3 | 5 | 5 | 5 | — |
| | 1 | 5 | 5 | 5 | — |
| 10 | 10 | 5 | 5 | 5 | + |
| | 3 | 5 | 5 | 5 | — |
| | 1 | 5 | 5 | 5 | — |
| Control compound 1 | 20 | 1 | 2 | 2 | — |
| | 10 | 0 | 1 | 1 | — |
| | 5 | 0 | 0 | 0 | — |
| Control compound 2 | 20 | 2 | 2 | 2 | — |
| | 10 | 1 | 1 | 1 | — |
| | 5 | 0 | 0 | 0 | — |
| Control compound 3 | 20 | 5 | 5 | 5 | + |
| | 10 | 4 | 4 | 5 | — |
| | 5 | 3 | 3 | 4 | — |

EXPERIMENTAL EXAMPLE 2

Herbicidal Effects of Soil Treatment on Field Weeds

Field soil was placed in vats having an area of 16×11 cm$^2$ and a depth of 7 cm, and seeds of *Echinochloa Crusgalli*, *Polygonum longisetum*, *Digitaria sanguinalis*, *Amaranthus sp*, *Chenopodium album*, Corn and Soybean were sown and then covered with the soil to a depth of 1 cm. The next day, predetermined amounts of a diluted emulsion prepared in accordance with Preparation Example 1 or a diluted solution of the wettable powder prepared in accordance with Preparation Example 1 were applied uniformly on the soil at an amount of 20 g, 10 g or 5 g of Compounds 1-10 and Control Compounds 1-3 per Are. On the 20th day after the treatment, the herbicidal effects on the test weeds and phytotoxicity to the corn and soybean were evaluated in the same manner in Experimental Example 1. The results obtained are shown in Table 5.

TABLE 5

| Test compound | Amount applied (g/Are) | Degree of herbicidal effect | | | | | Phytotoxicity | |
|---|---|---|---|---|---|---|---|---|
| | | E. Crusgalli | P. longisetum | D. sanguinalis | Amaranthus sp. | C. album | Corn | Soybean |
| 1 | 20 | 5 | 5 | 5 | 5 | 5 | + | ++ |
| | 10 | 5 | 5 | 5 | 5 | 5 | + | + |
| | 5 | 5 | 5 | 5 | 5 | 5 | — | — |
| | 2.5 | 4 | 5 | 5 | 5 | 5 | — | — |
| 2 | 20 | 5 | 5 | 5 | 5 | 5 | — | + |

TABLE 5-continued

| Test compound | Amount applied (g/Are) | Degree of herbicidal effect | | | | | Phytotoxicity | |
|---|---|---|---|---|---|---|---|---|
| | | E. Crusgalli | P. longisetum | D. sanguinalis | Amaranthus sp. | C. album | Corn | Soybean |
| | 10 | 5 | 5 | 4 | 5 | 4 | — | — |
| | 5 | 3 | 5 | 3 | 4 | 3 | — | — |
| | 2.5 | 2 | 3 | 2 | 3 | 2 | — | — |
| 3 | 20 | 5 | 5 | 5 | 5 | 5 | ++ | ++ |
| | 10 | 5 | 5 | 5 | 5 | 5 | + | + |
| | 5 | 4 | 5 | 5 | 5 | 5 | — | — |
| | 2.5 | 2 | 5 | 4 | 4 | 4 | — | — |
| 4 | 20 | 4 | 5 | 5 | 5 | 5 | + | + |
| | 10 | 2 | 5 | 5 | 5 | 5 | — | — |
| | 5 | 1 | 4 | 4 | 4 | 4 | — | — |
| | 2.5 | | | | | | | |
| 5 | 20 | 5 | 5 | 5 | 5 | 5 | — | + |
| | 10 | 4 | 5 | 4 | 5 | 5 | — | — |
| | 5 | 3 | 5 | 3 | 4 | 4 | — | — |
| | 2.5 | 2 | 4 | 2 | 3 | 3 | — | — |
| 6 | 20 | 5 | 5 | 5 | 5 | 5 | + | + |
| | 10 | 5 | 5 | 5 | 5 | 5 | — | + |
| | 5 | 3 | 5 | 4 | 5 | 5 | — | — |
| | 2.5 | 2 | 5 | 3 | 4 | 4 | — | — |
| 7 | 20 | 5 | 5 | 5 | 5 | 5 | + | + |
| | 10 | 4 | 5 | 4 | 5 | 5 | + | + |
| | 5 | 2 | 5 | 3 | 5 | 5 | — | — |
| | 2.5 | 1 | 4 | 2 | 4 | 4 | — | — |
| 8 | 20 | 5 | 5 | 5 | 5 | 5 | ++ | + |
| | 10 | 4 | 5 | 4 | 5 | 5 | + | — |
| | 5 | 3 | 4 | 3 | 5 | 4 | — | — |
| | 2.5 | 2 | 3 | 2 | 4 | 4 | — | — |
| 9 | 20 | 5 | 5 | 5 | 5 | 5 | + | + |
| | 10 | 4 | 5 | 5 | 5 | 5 | — | — |
| | 5 | 3 | 5 | 3 | 4 | 4 | — | — |
| | 2.5 | | | | | | | |
| 10 | 20 | 5 | 5 | 5 | 5 | 5 | ++ | ++ |
| | 10 | 4 | 5 | 5 | 5 | 5 | + | + |
| | 5 | 3 | 5 | 5 | 5 | 5 | — | — |
| | 2.5 | 2 | 5 | 4 | 5 | 5 | — | — |
| Control compound 1 | 20 | | 0 | 0 | 1 | | — | |
| | 10 | | 0 | 0 | 0 | | | |
| | 5 | | 0 | 0 | 0 | | | |
| Control compound 2 | 20 | | 0 | 0 | 1 | | — | |
| | 10 | | 0 | 0 | 0 | | | |
| | 5 | | 0 | 0 | 0 | | | |
| Control compound 3 | 20 | | 5 | 4 | 5 | | + | |
| | 10 | | 4 | 3 | 4 | | — | |
| | 5 | | 2 | 2 | 3 | | — | |

EXPERIMENTAL EXAMPLE 3

Herbicidal Effects on Field Weeds by Stalk and Leaves Treatment

Field soil was placed in Wagnel pots of 1/5000 Are, and seeds of corn and weeds such as *Chenopodium album*, *Amaranthus sp* and *Polygonum longisetum* were sown. After 20 days, predetermined amounts of a diluted emulsion prepared in accordance with Preparation Example 1 were sprayed uniformly on the stalk and leaves of the grown test plants in the amount of 100 liters per 10 Ares. On the 20th day after the treatment, the herbicidal effects on the test weeds and phytotoxicity to the corn plant were evaluated in the same manner as described in Experimental Example 1. The results obtained are shown in Table 6.

TABLE 6

| Test compound | Amount applied (ppm) | Degree of Herbicidal effect | | | Phytotoxicity to corn |
|---|---|---|---|---|---|
| | | C. album | Amaranthus sp. | P. longisetum | |
| 1 | 2000 | 5 | 5 | 5 | |
| | 1000 | 5 | 5 | 5 | + |
| | 500 | 4 | 5 | 5 | — |
| 2 | 2000 | 5 | 5 | 5 | |
| | 1000 | 5 | 5 | 5 | + |
| | 500 | 4 | 4 | 5 | — |
| 3 | 2000 | 5 | 5 | 5 | |
| | 1000 | 5 | 5 | 5 | |
| | 500 | 5 | 5 | 5 | + |
| 4 | 2000 | 5 | 5 | 5 | |
| | 1000 | 5 | 5 | 5 | + |
| | 500 | 4 | 4 | 4 | — |
| 5 | 2000 | 5 | 5 | 5 | + |
| | 1000 | 5 | 5 | 5 | + |
| | 500 | 4 | 4 | 5 | — |
| 6 | 2000 | 5 | 5 | 5 | |
| | 1000 | 5 | 5 | 5 | |
| | 500 | 4 | 5 | 5 | + |
| 7 | 2000 | 5 | 5 | 5 | |

TABLE 6-continued

| Test compound | Amount applied (ppm) | Degree of Herbicidal effect | | | Phyto- toxicity to corn |
|---|---|---|---|---|---|
| | | C. album | Amaranthus sp. | P. longisetum | |
| | 1000 | 5 | 5 | 5 | |
| | 500 | 5 | 5 | 5 | + |
| 8 | 2000 | 5 | 5 | 5 | |
| | 1000 | 5 | 5 | 5 | + |
| | 500 | 4 | 4 | 5 | − |
| 9 | 2000 | 5 | 5 | 5 | |
| | 1000 | 5 | 5 | 5 | + |
| | 500 | 4 | 5 | 5 | − |
| 10 | 2000 | 5 | 5 | 5 | |
| | 1000 | 5 | 5 | 5 | + |
| | 500 | 5 | 5 | 5 | − |
| Control compound 1 | 2000 | 2 | 2 | 3 | + |
| | 1000 | 2 | 1 | 2 | − |
| | 500 | 1 | 1 | 1 | − |
| Control compound 2 | 2000 | 3 | 3 | 4 | + |
| | 1000 | 1 | 2 | 3 | − |
| | 500 | 0 | 0 | 1 | − |
| Control compound 3 | 2000 | 5 | 5 | 5 | |
| | 1000 | 4 | 4 | 4 | + |
| | 500 | 4 | 3 | 3 | − |

What is claimed is:

1. An oxazolidinedione compound represented by the formula (I):

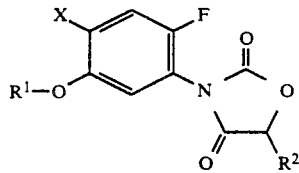

wherein $R^1$ represents an alkyl group having 3 carbon atoms, $R^2$ represents an alkyl group having 3 carbon atoms; and X represents a chlorine atom or a fluorine atom.

2. An oxazolidinedione compound as claimed in claim 1, wherein $R^1$ is selected from the group consisting of propyl and isopropyl and $R^2$ is selected from the group consisting of propyl and isopropyl and X is chlorine.

3. An oxazolidinedione compound as claimed in claim 1, wherein $R^1$ and $R^2$ are both isopropyl and X is chlorine.

4. A herbicidal composition which comprises an agriculturally acceptable carrier or diluent and a herbicidally effective amount of an oxazolidinedione compound represented by the formula:

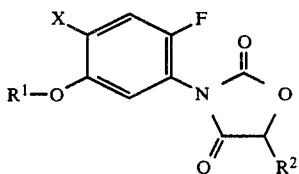

wherein $R^1$ represents an alkyl group having 3 carbon atoms, $R^2$ represents an alkyl group having 3 carbon atoms; and X represents a chlorine atom or a fluorine atom.

* * * * *